US007883713B2

(12) United States Patent
Betz et al.

(10) Patent No.: US 7,883,713 B2
(45) Date of Patent: Feb. 8, 2011

(54) TOPICAL APPLICATION OF THIAZOLYL AMIDES

(75) Inventors: Ulrich Betz, Reinheim (DE); Tobias Laich, Cologne (DE); Wolfgang Bender, Wuppertal (DE); Ruediger Fischer, Pulheim (DE); Martin Hendrix, Odenthal (DE); Gerald Kleymann, Bad-Salzuflen (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 899 days.

(21) Appl. No.: 10/481,680

(22) PCT Filed: Jun. 10, 2002

(86) PCT No.: PCT/EP02/06327

§ 371 (c)(1),
(2), (4) Date: Jun. 30, 2004

(87) PCT Pub. No.: WO03/000259

PCT Pub. Date: Jan. 3, 2003

(65) Prior Publication Data

US 2004/0235917 A1 Nov. 25, 2004

(30) Foreign Application Priority Data

Jun. 22, 2001 (DE) ................. 101 29 714

(51) Int. Cl.
*A61K 9/00* (2006.01)
*A61K 31/44* (2006.01)
(52) U.S. Cl. ...................... 424/400; 514/342
(58) Field of Classification Search ........... 514/369, 514/183, 336, 91, 342; 424/400
See application file for complete search history.

(56) References Cited

U.S. PATENT DOCUMENTS

| 3,658,830 | A |   | 4/1972 | Pilgram et al. |
| 3,717,651 | A |   | 2/1973 | Pilgram et al. |
| 3,847,588 | A |   | 11/1974 | Pilgram et al. |
| 4,556,560 | A | * | 12/1985 | Buckingham ............... 424/641 |
| 4,762,715 | A | * | 8/1988 | Lukas et al. ................ 424/642 |
| 5,034,382 | A | * | 7/1991 | Osswald ...................... 514/46 |
| 7,105,553 | B2 | * | 9/2006 | Fischer et al. ............... 514/369 |
| 2004/0006076 | A1 |   | 1/2004 | Fischer et al. |
| 2008/0220059 | A1 |   | 9/2008 | Laich et al. |

FOREIGN PATENT DOCUMENTS

| CA | 2 514 733 | 9/2004 |
| DE | 101 29 716 | 1/2003 |
| DE | 101 31 128 | 1/2003 |
| EP | 0 860 700 | 8/1998 |
| GB | 1323045 | 7/1973 |
| GB | 2311068 | 9/1997 |
| GB | 2311069 | 9/1997 |
| WO | WO-97/24343 | 7/1997 |
| WO | WO-97/36006 | 10/1997 |
| WO | WO-99/37291 | 7/1999 |
| WO | WO-99/42455 | 8/1999 |
| WO | WO-99/47507 | 9/1999 |
| WO | WO-00/53591 | 9/2000 |
| WO | 0147904 | 7/2001 |
| WO | 0196874 | 12/2001 |
| WO | WO-2004/078163 | 9/2004 |

OTHER PUBLICATIONS

The Merch Manual, Fifteenth edition, 1987, pp. 180-181.*
Kleymann, Gerald, et al., "New Helicase-primase Inhibitors as Drug Candidates for the Treatment of Herpes Simplex Disease", Nature Medicine, 8(4): 392-398 (Apr. 2002).
German Patent Application No. DE 101 29 716, filed on Jun. 22, 2001 (English Abstract Only).
German Patent Application No. DE 101 31 128, filed on Jun. 28, 2001 (English Abstract Only).
Translation of International Preliminary Report on Patentability for PCT/EP2006/002566, issued Oct. 3, 2007, 6 pages.
West, Solid state chemistry and its applications, Wiley, New York, (1988) pp. 358 and 365.
Vippagunta et al., Advanced Drug Delivery Reviews (2001) 48:3-26.
Crute et al., J. Med. Chem. (1995) 38(10):1820-1825.
Matthews et al., Antiviral Research (1993) 20:89-114.
Hantzsch, Chem. Ber. (1927) 60:2537-2545.
Artico et al., Eur. J. Med. Chem. (1992) 27:219-228.
Bartmann et al., J. Fluorine Chem. (1993) 61:117-122.
Ziegler and Spragus, J. Org. Chem., Am. Chem. Soc. (1960) 25:1454-1455.
Notice of Allowance from U.S. Appl. No. 10/168,197, mailed on Jul. 11, 2003.
Request for Continued Examination from U.S. Appl. No. 10/168,197, filed Oct. 16, 2003.
Non-Final Office Action from U.S. Appl. No. 10/168,197, mailed on Jan. 26, 2004.
Amendment from U.S. Appl. No. 10/168,197, filed Apr. 29, 2004.
Notice of Allowance from U.S. Appl. No. 10/168,197, mailed on Jul. 9, 2004.
Non-Final Office Action from U.S. Appl. No. 11/904,712, mailed on May 28, 2009.

* cited by examiner

*Primary Examiner*—Shengjun Wang
(74) *Attorney, Agent, or Firm*—Morrison & Foerster LLP

(57) ABSTRACT

The invention relates to the topical application of substituted thiazolyl amides in the treatment of herpes infections in humans, to preparations suitable for the topical application and to the production thereof.

5 Claims, No Drawings

TOPICAL APPLICATION OF THIAZOLYL AMIDES

The present invention relates to topical application of substituted thiazolylamides in the treatment of herpetic diseases in humans, to preparations suitable for topical use, and to the production thereof.

The active ingredients normally employed for the local therapy of herpes infections, especially HSV1 and HSV2, are nucleosidic, for example acyclovir. However, in many cases the therapy of the herpes infection is inadequate therewith.

The present invention relates to topically applicable preparations comprising from 0.1 to 99% by weight of a compound of the general formula (I)

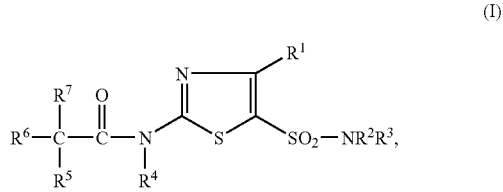

(I)

in which
$R^1$ is hydrogen, halogen, $(C_1-C_6)$-alkyl, $(C_1-C_6)$-alkoxy, amino-$(C_1-C_6)$-alkyl or halo-$(C_1-C_6)$-alkyl,
$R^2$ and $R^3$ are identical or different and are hydrogen, $(C_1-C_6)$-alkoxy, $(C_3-C_8)$-cycloalkyl or biphenylaminocarbonyl, or
are $(C_1-C_6)$-alkyl which is optionally substituted by 1 to 3 substituents which are selected from the group consisting of $(C_3-C_6)$-cycloalkyl, $(C_1-C_6)$-alkoxy, halogen, hydroxyl, amino, tri-$(C_1-C_6)$-alkylsilyloxy, radicals of the formula

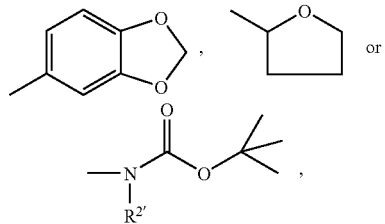

in which $R^{21}$ is hydrogen or $(C_1-C_4)$-alkyl,
a 5- to 6-membered aromatic heterocycle having up to 3 heteroatoms from the series S, N and/or O, where a nitrogen-containing heterocycle may also be bonded via the nitrogen atom,
a 3- to 8-membered saturated or unsaturated, nonaromatic, heterocycle which is optionally bonded via a nitrogen atom and has up to 3 heteroatoms from the series S, N and/or O, and
$(C_6-C_{10})$-aryl which may in turn be substituted by hydroxyl or $(C_1-C_6)$-alkoxy, or
are a group of the formula

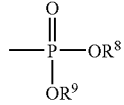

in which $R^8$ and $R^9$ are identical to or different from one another and are hydrogen and $(C_1-C_4)$-alkyl, or
are a group of the formula

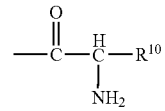

in which $R^{10}$ is the side group of a naturally occurring α-amino acid, or
is a group of the formula

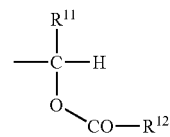

in which $R^{11}$ is $(C_1-C_4)$-alkyl, and $R^{12}$ is hydrogen, $(C_1-C_4)$-alkyl or a group of the formula

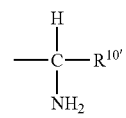

in which $R^{10'}$ is the side group of a naturally occurring α-amino acid, or
$R^2$ and $R^3$ form together with the nitrogen atom a 5- to 6-membered saturated heterocycle which may optionally also have an oxygen atom,
$R^4$ is hydrogen, $(C_1-C_6)$-acyl, $(C_2-C_6)$-alkenyl, $(C_3-C_8)$-cycloalkyl, or
$R^4$ is $(C_1-C_6)$-alkyl which be may optionally substituted by 1 to 3 substituents which are selected from the group consisting of halogen, hydroxyl, $(C_3-C_8)$-cycloalkyl, $(C_1-C_6)$-acyl, $(C_1-C_6)$-alkoxy, carboxyl,

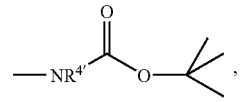

in which $R^{4'}$ is hydrogen,
—$(OCH_2CH_2)_nOCH_2CH_3$ in which n is 0 or I, phenoxy, $(C_6-C_{10})$-aryl and —$NR^{13}R^{14}$,
in which $R^{13}$ and $R^{14}$ are identical or different and are hydrogen, $(C_1-C_6)$-acyl, $(C_1-C_6)$-alkyl, carbamoyl, mono- or di$(C_1-C_6)$-alkylamino$(C_1-C_6)$-alkyl, mono- or di$(C_1-C_6)$-alkylaminocarbonyl, $(C_6-C_{10})$-aryl or $(C_1-C_6)$-alkoxycarbonyl or
$R^{13}$ and $R^{14}$ form together with the nitrogen atom a 5- to 6-membered saturated heterocycle which may optionally comprise a further heteroatom from the series S or O or a radical of the formula —$NR^{15}$, and may be substituted by oxo,
in which
$R^{15}$ is hydrogen or $(C_1-C_4)$-alkyl, or
$R^4$ is $(C_1-C_6)$-alkyl which is substituted by a 5- to 6-membered aromatic, optionally benzo-fused heterocycle having up to 3 heteroatoms from the series S, N and/or O, where a nitrogen atom containing heterocycle may also be bonded via the nitrogen atom, or is substituted by radicals of the formulae

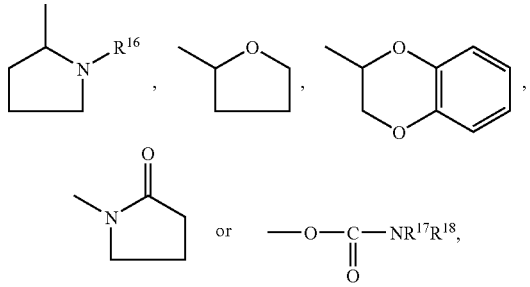

in which
$R^{16}$ is hydrogen or $(C_1-C_6)$-alkyl,
$R^{17}$ and $R^{18}$ are identical or different and are hydrogen, $(C_1-C_6)$-alkyl or $(C_6-C_{10})$-aryl, where aforementioned $(C_1-C_6)$-alkyl and $(C_6-C_{10})$-aryl may optionally be substituted by 1 to 3 substituents selected from the group consisting of hydroxyl, $(C_1-C_6)$-alkoxy and halogen,
$R^5$ is hydrogen, $(C_1-C_6)$-alkyl, halogen, amino, mono- or di$(C_1-C_6)$-alkylamino or is $(C_1-C_6)$-alkanoylamino,
$R^6$ is phenyl which may optionally be substituted by one to three substituents selected from the group consisting of halogen,
$(C_6-C_{10})$-aryl which may optionally be substituted by 1 to 3 substituents selected from $(C_1-C_6)$-alkanoyl, $(C_1-C_6)$-alkoxy, $(C_1-C_6)$-alkyl, halogen, $(C_1-C_6)$-alkoxycarbonyl, nitro, halo-$(C_1-C_6)$-lkyl, halo-$(C_1-C_6)$-alkoxy, amino, $(C_1-C_6)$-alkylthio, hydroxyl, carboxyl, carbamoyl, mono- or di-$(C_1-C_6)$-alkylaminocarbonyl, mono- or di-$(C_1-C_6)$-alkanoylamino, $(C_1-C_6)$-alkoxycarbonylamino, $(C_1-C_6)$-alkylsulfoxy, $(C_1-C_6)$-alkylsulfonyl, tri-$(C_1-C_6)$-alkylsilyloxy, a 3- to 8-membered, saturated, or unsaturated, nonaromatic, mono- or bicyclic heterocycle which is optionally bonded via a nitrogen atom and has up to 3 heteroatoms from the series S, N and/or O, and/or cyano,
$(C_1-C_6)$-alkoxy,
$(C_1-C_6)$-alkoxycarbonyl,
$(C_1-C_6)$-alkylthio,
hydroxyl,
carboxyl,
partially fluorinated $(C_1-C_6)$-alkoxy having up to 6 fluorine atoms,
$(C_1-C_6)$-alkyl which is optionally substituted by a radical of the formula

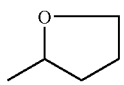

a 5- to 6-membered aromatic heterocycle which is optionally bonded via a nitrogen atom and carries up to 3 heteroatoms from the series S, N and/or 0 and which may optionally be substituted by 1 to 3 substituents selected from $(C_1-C_6)$-alkanoyl, $(C_1-C_6)$-alkoxy, $(C_1-C_6)$-alkyl, halogen, $(C_1-C_6)$-alkoxycarbonyl, nitro, halo-$(C_1-C_6)$-alkyl, halo-$(C_1-C_6)$-alkoxy, amino, $(C_1-C_6)$-alkylthio, hydroxyl, carboxyl, carbamoyl, aminocarbonyl, mono- or di-$(C_1-C_6)$-alkylaminocarbonyl, mono- or di-$(C_1-C_6)$-alkanoylamino, $(C_1-C_6)$-alkoxycarbonylamino, $(C_1-C_6)$-alkylsulfoxy, $(C_1-C_6)$-alkylsulfonyl, a 3- to 8-membered saturated or unsaturated, nonaromatic, mono- or bicyclic heterocycle which is optionally bonded via a nitrogen atom and has up to 3 heteroatoms from the series S, N and/or O, and/or cyano,
a 3- to 8-membered saturated or unsaturated, nonaromatic, mono- or bicyclic heterocycle which is optionally bonded via a nitrogen atom and has up to 3 heteroatoms from the series S, N and/or O, and which may optionally be substituted by 1 to 3 substituents selected from oxo, halogen, hydroxyl, $(C_1-C_6)$-alkoxycarbonyl, $(C_1-C_6)$-alkoxycarbonylamino, $(C_1-C_6)$-alkyl, halo-$(C_1-C_6)$-alkyl and hydroxy-$(C_1-C_6)$-alkyl,
$(C_2-C_6)$-alkenyl
and groups of the formulae
$OR^{19}$,
$—NR^{20}R^{21}$ or $—CO—NR^{22}R^{23}$,
carbazol, dibenzofuran or dibenzothiophene,
xanthene or 9,10-dihydroacridine,
in which $R^{19}$ is phenyl which in turn is optionally substituted by a group of the formula $—NR^{24}R^{25}$,
in which
$R^{24}$ and $R^{25}$ are identical or different and are hydrogen, $(C_1-C_6)$-alkyl or $(C_1-C_6)$-acyl, or
$R^{19}$ is $(C_1-C_6)$-alkyl which is optionally substituted once to three times by hydroxyl and/or halogen,
$R^{20}$ and $R^{21}$ are identical or different and are hydrogen, carbamoyl, mono- or di-$(C_1-C_6)$-alkylaminocarbonyl, phenyl, $(C_1-C_6)$-acyl or $(C_1-C_6)$-alkyl,
where aforementioned $(C_1-C_6)$-alkyl is optionally substituted by $(C_1-C_6)$-alkoxy, $(C_1-C_6)$-acyl, by phenyl or by a 5- to 6-membered aromatic heterocycle having up to 3 heteroatoms from the series S, N and/or O,
where aforementioned phenyl and aforementioned aromatic heterocycle are optionally substituted once to three times, identically or differently, by halogen and/or hydroxyl, and
$R^{22}$ and $R^{23}$ are identical or different and are hydrogen or $(C_1-C_6)$-alkyl,
and $R^7$ may have the meaning of $R^5$ and may be identical to or different from the latter,
and the salts thereof.

The compounds can be applied in the topically applicable preparations as such or as salt with an acid or base. Use as prodrug, for example of esters, is also possible.

Physiologically acceptable salts of the compounds of the invention may be for example salts of the substances of the invention with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid.

Further salts which may be mentioned are salts with conventional bases, such as, for example, alkali metal salts (e.g. sodium or potassium salts), alkaline earth metal salts (e.g. calcium or magnesium salts) or ammonium salts derived from ammonia or organic amines such as, for example, diethylamine, triethylamine, ethyldiisopropylamine, procaine, dibenzylamine, N-methylmorpholine, dihydroabietylamine, 1-ephenamine or methylpiperidine.

The compounds of the invention may, depending on the substitution pattern, exist in stereoisomeric forms which either are related as image and mirror image (enantiomers), or are not related as image and mirror image (diastereomers). The invention relates either to the enantiomers or diastereomers or respective mixtures thereof. The racemic forms can, just like the diastereomers, be separated in a known manner into the stereoisomerically pure constituents.

$(C_1-C_6)$-Alkyl is expediently a straight-chain or branched alkyl radical having 1 to 6 carbon atoms. A straight-chain or branched alkyl radical having 1 to 4 carbon atoms $(C_1-C_4)$ is preferred. Examples which may be mentioned are: methyl, ethyl, n-propyl, isopropyl, n-butyl, sec-butyl, tert-butyl, n-pentyl and n-hexyl. A straight-chain or branched alkyl radical having 1 to 3 carbon atoms ($(C_1-C_3)$-alkyl) is particularly preferred.

Halo$(C_1-C_6)$-alkyl is expediently a $(C_1-C_6)$-alkyl group which may be defined as above and which has 1 to 3 halogen atoms, namely F, Cl, Br and/or I, preferably chlorine or fluorine as substituents, examples which may be mentioned being trifluoromethyl, fluoromethyl etc.

Hydroxy$(C_1-C_6)$-alkyl is expediently a $(C_1-C_6)$-alkyl group which may be defined as above and which has 1 to 3 hydroxyl groups as substituents, examples which may be mentioned being hydroxymethyl etc.

$(C_2-C_6)$-Alkenyl is for the purposes of the invention expediently a straight-chain or branched alkenyl radical having 2 to 6 carbon atoms. Examples which may be mentioned are: ethenyl, n-prop-2-en-1-yl and n-but-2-en-1-yl. A straight-chain or branched alkenyl radical having 2 to 4 carbon atoms is preferred.

$C_1-C_6$-Alkoxy is expediently a straight-chain or branched alkoxy radical having 1 to 6 carbon atoms. A straight-chain or branched alkoxy radical having 1 to 4 carbon atoms $(C_1-C_4)$ is preferred. Examples which may be mentioned are: methoxy, ethoxy, n-propoxy, isopropoxy, tert-butoxy, n-pentoxy and n-hexoxy. A straight-chain or branched alkoxy radical having 1 to 3 carbon atoms $(C_1-C_3)$ is particularly preferred.

Halo-$(C_1-C_6)$-alkoxy is expediently mono- or polyhalo-substituted $(C_1-C_6)$-alkoxy. Reference may be made to the above definition concerning the $(C_1-C_6)$-alkoxy portion, and the definition of halogen. For example, halo-$(C_1-C_6)$-alkoxy includes $(C_1-C_6)$-alkoxy which is partially chlorinated and/or fluorinated one or more times, or perfluorinated, such as trifluoromethoxy, fluoromethoxy, chloromethoxy, pentafluoroethoxy, trifluoromethylmethoxy etc.

Partially fluorinated $(C_1-C_6)$-alkoxy having up to 6 fluorine atoms is expediently a straight-chain or branched alkoxy radical which has 1 to 6 carbon atoms and which may be substituted by 1 to 6, preferably 1 to 4, more preferably 1 to 3 fluorine atoms. A straight-chain or branched alkoxy radical having 1 to 4 carbon atoms and 1 to 4 fluorine atoms is preferred. Examples which may be mentioned are: methoxy, ethoxy, n-propoxy, isopropoxy, tert-butoxy, n-pentoxy and n-hexoxy, each of which has 1 to 4 fluorine atoms. (1,3-Difluoroprop-2-yl)oxy and 1,1,2,2-tetrafluoroethoxy are particularly preferred.

$(C_1-C_6)$-Alkylthio is expediently a straight-chain or branched alkylthio radical having 1 to 6 carbon atoms. A straight-chain or branched alkylthio radical having 1 to 4 carbon atoms $(C_1-C_4)$ is preferred. Examples which may be mentioned are: methylthio, ethylthio, n-propylthio, isopropylthio, tert-butylthio, n-pentylthio and n-hexylthio. A straight-chain or branched alkylthio radical having 1 to 3 carbon atoms $(C_1-C_3)$ is particularly preferred.

$(C_1-C_6)$-Alkoxycarbonyl is expediently a straight-chain or branched alkoxycarbonyl radical having 1 to 6 carbon atoms. A straight-chain or branched alkoxycarbonyl radical having 1 to 4 carbon atoms $(C_1-C_4)$ is preferred. Examples which may be mentioned are: methoxycarbonyl, ethoxycarbonyl, n-propoxycarbonyl, isopropoxycarbonyl and tert-butoxycarbonyl. A straight-chain or branched alkoxycarbonyl radical having 1 to 4 carbon atoms $(C_1-C_4)$ is particularly preferred.

Mono- or di-$(C_1-C_6)$-alkylaminocarbonyl expediently for the purposes of the invention is expediently a carbamoyl group ($H_2N$—CO—), in which one or both hydrogen atoms are replaced by a $(C_1-C_6)$-alkyl group. Concerning the definition of the $(C_1-C_6)$-alkyl group, reference may be made to the above explanation of $(C_1-C_6)$-alkyl. Methylaminocarbonyl, dimethylaminocarbonyl etc. may be mentioned as examples.

Mono- or di-$(C_1-C_6)$-acylamino for the purposes of the invention is expediently an amino group ($H_2N$—), in which one or both hydrogen atoms are replaced by a $(C_1-C_6)$-acyl group. Concerning the definition of the $(C_1-C_6)$-acyl group, reference may be made to the explanation of $(C_1-C_6)$-acyl above. $(C_1-C_6)$-Alkanoyl as mentioned in the definition of $(C_1-C_6)$-acyl may be mentioned by way of example.

$(C_1-C_6)$-Alkylsulfoxy is expediently a $(C_1-C_6)$-alkyl-S(=O) group and, concerning the $(C_1-C_6)$-alkyl group, reference may be made to the definition thereof above.

$(C_1-C_6)$-Alkylsulfonyl is expediently a $(C_1-C_6)$-alkyl-$SO_2$ group and, concerning the $(C_1-C_6)$-alkyl group, reference may be made to the definition thereof above.

$(C_6-C_{10})$-yl is generally an aromatic radical having 6 to 10 carbon atoms. Preferred aryl radicals are phenyl and naphthyl.

$(C_1-C_6)$-Acyl is for the purposes of the invention expediently a straight-chain or branched acyl radical having 1 to 6 carbon atoms. Examples which may be mentioned are: formyl, acetyl, ethanoyl, propanoyl, isopropanoyl, butanoyl, isobutanoyl and pentanoyl. A straight-chain or branched acyl radical having 1 to 4 carbon atoms is preferred. Acetyl and ethanoyl are particularly preferred.

$(C_3-C_8)$-Cycloalkyl is for the purposes of the invention cyclopropyl, cyclopentyl, cyclobutyl, cyclohexyl, cycloheptyl or cyclooctyl. Those which may be mentioned as preferred are: cyclopropyl, cyclopentyl or cyclohexyl. The meaning of $(C_3-C_6)$-cycloalkyl correspondingly is expediently cyclopropyl, cyclopentyl, cyclobutyl, cyclohexyl.

Halogen is for the purposes of the invention generally fluorine, chlorine, bromine and iodine. Fluorine, chlorine and bromine are preferred. Fluorine and chlorine are particularly preferred.

$(C_1-C_6)$-Alkanoyl is for the purposes of the invention formyl and $(C_1-C_5)$-alkylcarbonyl groups, $(C_1-C_5)$-alkyl may be a straight-chain or branched-chain alkyl group having 1 to 5 carbon atoms, for example acetyl, propionyl, butyryl, pentanoyl.

A 5- to 6-membered aromatic heterocycle having up to 3 heteroatoms from the series S, O and/or N is, for example, pyridyl, pyrimidyl, thienyl, furyl, pyrrolyl, thiazolyl, N-triazolyl, oxazolyl or imidazolyl. Pyridyl, furyl, thiazolyl and N-triazolyl are preferred.

A 5- to 6-membered aromatic benzo-fused heterocycle having up to 3 heteroatoms from the series S, O and/or N is, for example, benzimidazolyl.

A 5- to 6-membered saturated heterocycle which is bonded via a nitrogen atom, which may be formed from two substituent groups together with the nitrogen atom to which they are bonded, and which may optionally contain a further heteroatom from the series S or O or a radical of the formula —$NR^{15}$ in which $R^{15}$ is as defined above, is for the purposes of the invention generally morpholinyl, piperidinyl, piperazinyl, methylpiperazinyl, thiomorpholinyl or pyrrolidinyl. Morpholinyl, piperidinyl, pyrrolidinyl and thiomorpholinyl are particularly preferred.

A 3- to 8-membered saturated or unsaturated, nonaromatic heterocycle which is bonded via a nitrogen atom and has up to 3 heteroatoms from the series S, N and/or O includes for example the abovementioned 5- to 6-membered saturated heterocycles bonded via a nitrogen atom, and 3-, 7- and 8-membered heterocycles such as, for example, aziridines (e.g. 1-azacyclopropan-1-yl), azetidines (e.g. 1-azacyclobutan-1-yl) and azepines (e.g. 1-azepan-1-yl). The unsaturated representatives may comprise 1 to 2 double bonds in the ring.

The side group of a naturally occurring α-amino acid in the meaning of $R^{10}$ includes for example: hydrogen (glycine), methyl (alanine), propan-2-yl (valine), 2-methylpropan-1-yl (leucine), 1-methylpropan-1-yl (isoleucine), a propane-1,3-diyl group which is connected to the nitrogen atom of the amino group (proline), a 2-hydroxypropane-1,3-diyl group which is connected to the nitrogen atom of the amino group (hydroxyproline), a group of the formula

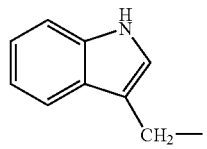

(tryptophan), a benzyl group (phenylalanine), a methylthioethyl group (methionine), hydroxymethyl (serine), p-hydroxybenzyl (tyrosine), 1-hydroxyethan-1-yl (threonine), mercaptomethyl (cysteine), carbamoylmethyl (asparagine), carbamoylethyl (glutamine), carboxymethyl (aspartic acid), carboxyethyl (glutamic acid), 4-aminobutan-1-yl (lysine), 3-guanidinopropan-1-yl (arginine), imidazol-4-ylmethyl (histidine), 3-ureidopropan-1-yl (citrulline), mercaptoethyl (homocysteine), hydroxyethyl (homoserine), 4-amino-3-hydroxybutan-1-yl (hydroxylysine), 3-aminopropan-1-yl (ornithine), etc.

The compounds are applied topically in the form of the topically applicable preparations for the treatment or prophylaxis of infections and diseases of the skin with herpes, in particular herpes simplex, especially HSV1 and HSV2. Treatment or prophylaxis of deeper-lying or systemic infections is also possible through topical application of the compounds when the bioavailability is sufficient.

The topically applicable preparations of the invention comprise 0.1 to 99, preferably 0.5 to 20% by weight of active ingredient of the formula (I). The topically applicable preparations of the invention particularly preferably comprise 1 to 5% by weight of active ingredient of the formula (I), in particular 2 to 3% by weight of active ingredient.

In one embodiment, the present invention relates to suspensions and ointments for topical application which comprise the active ingredient of the formula (I).

Further topical preparations of the invention include solutions, sprays, lotions, gels, creams, powders, powder sprays, pastes, emulsions, foams and sticks which comprise the active ingredient of the formula (I), where appropriate also a plurality of active ingredients.

Topical application of the present formula (I) also takes place in the form of plasters, foam-dressing sprays, occlusive dressings, compresses and controlled delivery systems.

The active ingredients may be present in these preparations in dissolved or suspended form.

Ointments comprise hydrocarbon gels, lipogels, absorption bases, W/O ointment bases, mixed emulsions or polyethylene glycols as base.

Creams comprise O/W bases.

Pastes comprise large amounts of powdered ingredients such as, for example, zinc oxide, talc, starch or titanium dioxide, besides an ointment or cream base.

Gels comprise solvents such as water, ethanol, isopropanol or propylene glycol and are produced using gel formers such as cellulose ethers, alginates, polyacrylates, bentonite, gelatin, tragacanth, polyvinylpyrrolidone or polyvinyl alcohol. Lipophilic gel bases or microemulsions can also be used.

Powders comprise powdered additives such as starch, stearates, silica, clay, magnesium carbonate, talc, cellulose, zinc oxide and, in particular, lactose.

It is possible to add stabilizers, antioxidants, preservatives, humectants, superfatting agents, solvents or excipients to improve penetration and efficacy to all the preparations.

Examples of penetration improvers are propylene glycol, polyethylene glycol, dimethyl sulfoxide, decyl methyl sulfoxide, azone, N-methylpyrrolidone, diethyltoluamide, ethanol, isopropyl myristate, isopropyl palmitate, oleic acid and its esters, medium chain-length triglycerides, dimethylisosorbitol, 2-octyldodecanol, branched-chain fatty acid esters, benzyl alcohol, urea, salicylates and surfactants.

In a further embodiment, the invention relates to compounds of the general formula (I) as claimed in claim 1:

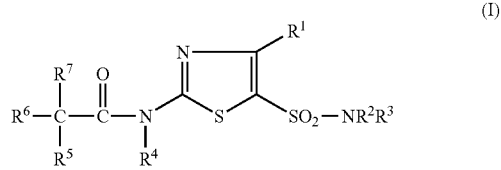

in which $R^1$ is hydrogen, halogen, $(C_1-C_6)$-alkyl, $(C_1-C_6)$-alkoxy, amino-$(C_1-C_6)$-alkyl or halo-$(C_1-C_6)$-alkyl, $R^2$ and $R^3$ are identical or different and are hydrogen, $(C_1-C_6)$-alkoxy, $(C_3-C_8)$-cycloalkyl or biphenylaminocarbonyl, or are $(C_1-C_6)$-alkyl which is optionally substituted by 1 to 3 substituents which are selected from the group consisting of $(C_3-C_6)$-cycloalkyl, $(C_1-C_6)$-alkoxy, halogen, hydroxyl, amino, radicals of the formula

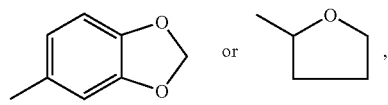

a 5- to 6-membered aromatic heterocycle having up to 3 heteroatoms from the series S, N and/or O, where a nitrogen-containing heterocycle may also be bonded via the nitrogen atom, a 3- to 8-membered saturated or unsaturated, nonaromatic, heterocycle which is optionally bonded via a nitrogen atom and has up to 3 heteroatoms from the series S, N and/or O, and ($C_6$-$C_{10}$)-aryl which may in turn be substituted by hydroxyl or ($C_1$-$C_6$)-alkoxy, or
are a group of the formula

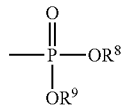

in which $R^8$ and $R^9$ are identical to or different from one another and are hydrogen and ($C_1$-$C_4$)-alkyl, or
are a group of the formula

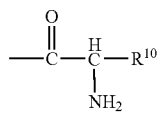

in which $R^{10}$ is the side group of a naturally occuring α-amino acid, or
is a group of the formula

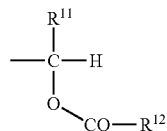

in which $R^{11}$ is ($C_1$-$C_4$)-alkyl, and $R^{12}$ is hydrogen, ($C_1$-$C_4$)-alkyl or a group of the formula

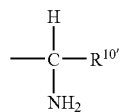

in which $R^{10'}$ is the side group of a naturally occurring α-amino acid, or
$R^2$ and $R^3$ form together with the nitrogen atom a 5- to 6-membered saturated heterocycle which may optionally also have an oxygen atom,
$R^4$ is hydrogen, ($C_1$-$C_6$)-acyl, ($C_2$-$C_6$)-alkenyl, ($C_3$-$C_8$)-cycloalkyl, or
$R^4$ is ($C_1$-$C_6$)-alkyl which may optionally be substituted by 1 to 3 substituents which are selected from the group consisting of halogen, hydroxyl, ($C_1$-$C_6$)-acyl, ($C_1$-$C_6$)-alkoxy,
—(OCH$_2$CH$_2$)$_n$OCH$_2$CH$_3$ in which n is 0 or 1, phenoxy, ($C_6$-$C_{10}$)-aryl and —NR$^{13}$R$^{14}$,
in which
$R^{13}$ and $R^{14}$ are identical or different and are hydrogen, ($C_1$-$C_6$)-acyl, ($C_1$-$C_6$)-alkyl, carbamoyl, mono- or di($C_1$-$C_6$)-alkylamino($C_1$-$C_6$)-alkyl, mono- or di($C_1$-$C_6$)-alkylaminocarbonyl, ($C_6$-$C_{10}$)-aryl or ($C_1$-$C_6$)-alkoxycarbonyl, or
$R^{13}$ and $R^{14}$ form together with the nitrogen atom a 5- to 6-membered saturated heterocycle which may optionally comprise a further heteroatom from the series S or O or a radical of the formula —NR$^{15}$, and may be substituted by oxo,
in which R$^{15}$ is hydrogen or ($C_1$-$C_4$)-alkyl, or
$R^4$ is ($C_1$-$C_6$)-alkyl which is substituted by a 5- to 6-membered aromatic, optionally benzo-fused heterocycle having up to 3 heteroatoms from the series S, N and/or O, where a nitrogen atom containing heterocycle may also be bonded via the nitrogen atom, or is substituted by radicals of the formulae

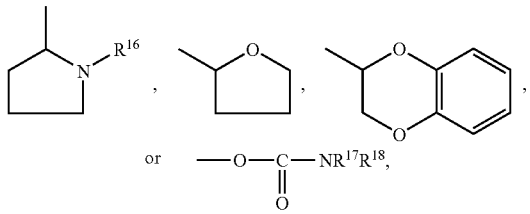

in which
$R^{16}$ is hydrogen ($C_1$-$C_6$)-alkyl,
$R^{17}$ and $R^{18}$ are identical or different and are hydrogen, ($C_1$-$C_6$)-alkyl or ($C_6$-$C_{10}$)-aryl, where aforementioned ($C_1$-$C_6$)-alkyl and ($C_6$-$C_{10}$)-aryl may optionally be substituted by 1 to 3 substituents selected from the group consisting of hydroxyl, ($C_1$-$C_6$)-alkoxy and halogen,
$R^5$ is hydrogen, ($C_1$-$C_6$)-alkyl, halogen, amino, mono- or di($C_1$-$C_6$)-alkylamino or is ($C_1$-$C_6$)-alkanoylamino,
$R^6$ is phenyl which may optionally be substituted by one to three substituents selected from the group consisting of halogen,
($C_6$-$C_{10}$)-aryl which may optionally be substituted by 1 to 3 substituents selected from ($C_1$-$C_6$)-alkanoyl, ($C_1$-$C_6$)-alkoxy, ($C_1$-$C_6$)-alkyl, halogen, ($C_1$-$C_6$)-alkoxycarbonyl, nitro, halo-($C_1$-$C_6$)-alkyl, halo-($C_1$-$C_6$)-alkoxy, amino, ($C_1$-$C_6$)-alkylthio, hydroxyl, carboxyl, carbamoyl, mono- or di-($C_1$-$C_6$)-alkylaminocarbonyl, mono- or di-($C_1$-$C_6$)-alkanoylamino, ($C_1$-$C_6$)-alkoxycarbonylamino, ($C_1$-$C_6$)-alkylsulfoxy, ($C_1$-$C_6$)-alkylsulfonyl, tri-($C_1$-$C_6$)-alkylsilyloxy, a 3- to 8-membered, saturated, or unsaturated, nonaromatic, mono- or bicyclic heterocycle which is optionally bonded via a nitrogen atom and has up to 3 heteroatoms from the series S, N and/or O, and/or cyano,
($C_1$-$C_6$)-alkoxy,
($C_1$-$C_6$)-alkoxycarbonyl,
($C_1$-$C_6$)-alkylthio,
hydroxyl,
carboxyl,
partially fluorinated ($C_1$-$C_6$)-alkoxy having up to 6 fluorine atoms,
($C_1$-$C_6$)-alkyl which is optionally substituted by a radical of the formula

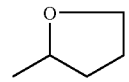

a 5- to 6-membered aromatic heterocycle which is optionally bonded via a nitrogen atom and carries up to 3 heteroatoms from the series S, N and/or 0 and which may optionally be substituted by 1 to 3 substituents selected from ($C_1$-$C_6$)-alkanoyl, ($C_1$-$C_6$)-alkoxy, ($C_1$-$C_6$)-alkyl, halogen, ($C_1$-$C_6$)-alkoxycarbonyl, nitro, halo-$(C_1-C_6)$-alkyl, halo-$(C_1-C_6)$-alkoxy, amino, $(C_1-C_6)$-alkylthio, hydroxyl, carboxyl, carbamoyl, mono- or di-$(C_1-C_6)$-alkylaminocarbonyl, mono- or di-$(C_1-C_6)$-alkanoylamino, $(C_1-C_6)$-alkoxycarbonylamino, $(C_1-C_6)$-alkylsulfoxy, $(C_1-C_6)$-alkylsulfonyl, a 3- to 8-membered saturated or unsaturated, nonaromatic, mono- or bicyclic heterocycle which is optionally bonded via a nitrogen atom and has up to 3 heteroatoms from the series S, N and/or O, and/or cyano, a 3- to 8-membered saturated or unsaturated, nonaromatic, mono- or bicyclic heterocycle which is optionally bonded via a nitrogen atom and has up to 3 heteroatoms from the series S, N and/or O, and which may optionally be substituted by 1 to 3 substituents selected from oxo, halogen, hydroxyl, $(C_1-C_6)$-alkoxycarbonyl, $(C_1-C_6)$-alkoxycarbonyl amino, $(C_1-C_6)$-alkyl, halo-$(C_1-C_6)$-alkyl and hydroxy-$(C_1-C_6)$-alkyl, and groups of the formulae
$OR^{19}$,
$-NR^{20}R^{21}$ or $-CO-NR^{22}R^{23}$,
in which
$R^{19}$ is phenyl which in turn is optionally substituted by a group of the formula $-NR^{24}R^{25}$,
in which
$R^{24}$ and $R^{25}$ are identical or different and are hydrogen, $(C_1-C_6)$-alkyl or $(C_1-C_6)$-acyl, or
$R^{19}$ is $(C_1-C_6)$-alkyl which is optionally substituted once to three times by hydroxyl and/or halogen,
$R^{20}$ and $R^{21}$ are identical or different and are hydrogen, carbamoyl, mono- or di-$(C_1-C_6)$-alkylaminocarbonyl, phenyl, $(C_1-C_6)$-acyl or $(C_1-C_6)$-alkyl,
where aforementioned $(C_1-C_6)$-alkyl is optionally substituted by $(C_1-C_6)$-alkoxy, $(C_1-C_6)$-acyl, by phenyl or by a 5- to 6-membered aromatic heterocycle having up to 3 heteroatoms from the series S, N and/or O,
where aforementioned phenyl and aforementioned aromatic heterocycle are optionally substituted once to three times, identically or differently, by halogen and/or hydroxyl, and
$R^{22}$ and $R^{23}$ are identical or different and are hydrogen or $(C_1-C_6)$-alkyl, and $R^7$ may have the meaning of $R^5$ and may be identical to or different from the latter, and the salts thereof.

In a preferred embodiment, the invention relates to compounds of the general formula (I) 1 in which $R^1$ is hydrogen or $(C_1-C_6)$-alkyl, in particular methyl.

In a further preferred embodiment, the invention relates to compounds of the general formula (I) in which $R^2$ and $R^3$ are each independently hydrogen, $(C_1-C_6)$-alkyl or 2-hydroxyethyl, in particular hydrogen, methyl and 2-hydroxyethyl.

In a further preferred embodiment, the invention relates to compounds of the general formula (I) in which $R^2$ is hydrogen and $R^3$ is $(C_1-C_6)$-alkoxy or $(C_3-C_8)$-cycloalkyl, or
is $(C_1-C_6)$-alkyl which is optionally substituted by 1 to 3 substituents selected from the group consisting of $(C_3-C_6)$-cycloalkyl, $(C_1-C_6)$-alkoxy, halogen, hydroxyl, amino, tri-$(C_1-C_6)$-alkylsilyloxy,
a 5- to 6-membered aromatic heterocycle having up to 3 heteroatoms from the series S, N and/or O, where a nitrogen-containing heterocycle may also be bonded via the nitrogen atom,
a 3- to 8-membered saturated or unsaturated, nonaromatic, heterocycle which is optionally bonded via a nitrogen atom and has up to 3 heteroatoms from the series S, N and/or O, and $(C_6-C_{10})$-aryl which in turn may be substituted by hydroxyl or $(C_1-C_6)$-alkoxy, or
in a further preferred embodiment, the invention relates to compounds of the general formula (I) in which $R^4$ is hydrogen or $(C_1-C_6)$-alkyl, in particular methyl.

In a further preferred embodiment, the invention relates to compounds of the general formula (I) in which $R^5$ is hydrogen.

In a further preferred embodiment, the invention relates to compounds of the general formula (I) in which
$R^6$ is phenyl which may optionally be substituted by one to three substituents selected from the group consisting of halogen,
$(C_6-C_{10})$-aryl which may optionally be substituted by 1 to 3 substituents selected from $(C_1-C_6)$-alkanoyl, $(C_1-C_6)$-alkoxy, $(C_1-C_6)$-alkyl, halogen, $(C_1-C_6)$-alkoxycarbonyl, nitro, halo-$(C_1-C_6)$-alkyl, halo-$(C_1-C_6)$-alkoxy, amino, hydroxyl, mono- or di-$(C_1-C_6)$-alkylamino, mono- or di-$(C_1-C_6)$-alkanoylamino, $(C_1-C_6)$-alkoxycarbonylamino, and/or cyano, and
a 5- to 6-membered aromatic heterocycle which is optionally bonded via a nitrogen atom and has up to 3 heteroatoms from the series S, N and/or O and which may optionally be substituted by 1 to 2 halogen atoms.

In particular, $R^6$ is 1,1'-biphenyl-4-yl, 4-(2-pyridylphenyl) or 4-(1H-pyrazol-1-yl)phenyl, it being possible for these radicals to be substituted by 1 to 2 fluorine atoms. In a further preferred embodiment, the invention relates to compounds which have the following formula:

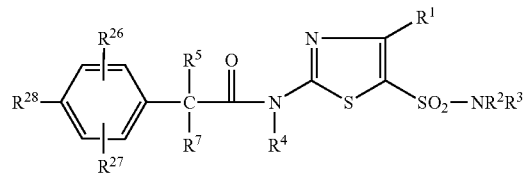

in which
$R^1$, $R^2$, $R^3$, $R^4$, $R^5$ and $R^7$ are as defined in claim 1,
$R^{26}$ and $R^{27}$ are identical or different and are hydrogen, halogen, $(C_1-C_6)$-alkoxy, $(C_1-C_6)$-alkoxycarbonyl, $(C_1-C_6)$-alkylthio, hydroxyl, carboxyl, partially fluorinated $(C_1-C_6)$-alkoxy having up to 6 fluorine atoms, $(C_1-C_6)$-alkyl, a group of the formulae $-OR^{19}$, $-NR^{20}R^{21}$ or $-CO-NR^{22}R^{23}$, in which
$R^{19}$ is phenyl which is in turn optionally substituted by a group of the formula $-NR^{24}R^{25}$,
in which
$R^{24}$ and $R^{25}$ are identical or different and are hydrogen, $(C_1-C_6)$-alkyl or $(C_1-C_6)$-acyl, or
$R^{19}$ is $(C_1-C_6)$-alkyl which is optionally substituted once to three times by hydroxyl and/or halogen,
$R^{20}$ and $R^{21}$ are identical or different and are hydrogen, carbamoyl, mono- or di-$(C_1-C_6)$-alkylaminocarbonyl, phenyl, $(C_1-C_6)$-acyl or $(C_1-C_6)$-alkyl,
where aforementioned $(C_1-C_6)$-alkyl is optionally substituted by $(C_1-C_6)$-alkoxy, $(C_1-C_6)$-acyl, phenyl or by a 5- to 6-membered aromatic heterocycle having up to 3 heteroatoms from the series S, N and/or O,
where aforementioned phenyl and aforementioned aromatic heterocycle are optionally substituted once to three times identically or differently by halogen and/or hydroxyl, and $R^{22}$ and $R^{23}$ are identical or different and are hydrogen or $(C_1-C_6)$-alkyl, $R^{28}$ is $(C_6-C_{10})$-aryl which may optionally be substituted by 1 to 3 substituents selected from $(C_1-C_6)$-alkanoyl, $(C_1-C_6)$-alkoxy, $(C_1-C_6)$-alkyl, halogen, $(C_1-C_6)$-alkoxycarbonyl, nitro, halo-$(C_1-C_6)$-alkyl, halo-$(C_1-C_6)$-alkoxy, amino, $(C_1-C_6)$-alkylthio, hydroxyl, carboxyl, carbamoyl, mono- or di-$(C_1-C_6)$-alkylaminocarbonyl, mono- or di-$(C_1-C_6)$-alkanoylamino, $(C_1-C_6)$-alkoxycarbonylamino, $(C_1-C_6)$-alkylsulfoxy, $(C_1-C_6)$-alkylsulfonyl, tri-$(C_1-C_6)$-alkylsilyloxy, a 3- to 8-membered saturated or unsaturated, nonaromatic, mono- or bicyclic heterocycle which is optionally bonded via a nitrogen atom and has up to 3 heteroatoms from the series S, N and/or O, and/or cyano, or $R^{28}$ is a 5- to 6-membered aromatic heterocycle which is optionally bonded via a nitrogen atom and has up to 3 heteroatoms from the series S, N and/or O, and which may optionally be substituted by 1 to 3 substituents selected from $(C_1-C_6)$-alkanoyl, $(C_1-C_6)$-alkoxy, $(C_1-C_6)$-alkyl, halogen, $(C_1-C_6)$-alkoxycarbonyl, nitro, halo-$(C_1-C_6)$-alkyl, halo-$C_1-C_6)$-alkoxy, amino, $(C_1-C_6)$-alkylthio, hydroxyl, carboxyl, carbamoyl, mono- or di-$(C_1-C_6)$-alkylaminocarbonyl, mono- or di-$(C_1-C_6)$-alkanoylamino, $(C_1-C_6)$-alkoxycarbonylamino, $(C_1-C_6)$-alkylsulfoxy, $(C_1-C_6)$-alkylsulfonyl, a 3- to 8-membered saturated or unsaturated, nonaromatic, mono- or bicyclic heterocycle which is optionally bonded via a nitrogen atom and has up to 3 heteroatoms from the series S, N and/or O, and/or cyano, and the salts thereof.

The compounds of the general formul (I) can be prepared by

[A] reacting compounds of the general formula (II)

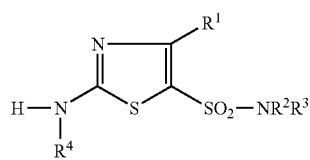

(II)

in which $R^1$, $R^2$, $R^3$ and $R^4$ have the abovementioned meaning, with compounds of the general formula (III)

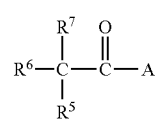

(III)

in which

A is a leaving group such as, for example, halogen, preferably chlorine, or hydroxyl, and $R^5$, $R^6$ and $R^7$ have the abovementioned meaning, in inert solvents, where appropriate in the presence of a base and/or of an auxiliary to give compounds of the formula (I),

[B] reacting compounds of the general formula (IV)

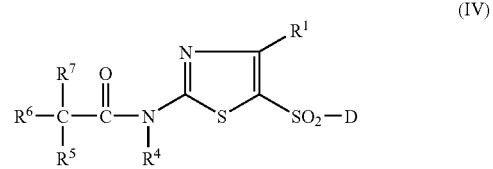

(IV)

in which $R^1$, $R^4$, $R^5$, $R^6$ and $R^7$ have the abovementioned meaning, and D is a halogen atom, preferably chlorine, with amines of the general formula (V):

$HNR^2R^3$ (V)

in which $R^2$ and $R^3$ have the abovementioned meaning, in inert solvents to give compounds of the formula (I),

[C] reacting compounds of the general formula (X)

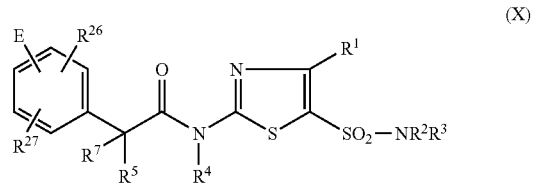

(X)

in which $R^1$, $R^2$, $R^3$, $R^4$, $R^5$, $R^7$, $R^{26}$ and $R^{27}$ have the abovementioned meaning, and E is trifluoromethanesulfonate or halogen, preferably bromine or iodine, with boronic acids or stannanes of the general formula (XI):

$R^{28}M$ (XI)

in which $R^{28}$ has the abovementioned meaning, and M can be for example a tri$(C_1-C_6)$-alkylstannyl group, such as a trimethylstannyl group or a boronic acid group, in inert solvents in the presence of palladium catalysts, e.g. tetrakis(triphenylphosphane)palladium (0), where appropriate in the presence of base, e.g. potassium phosphate at temperatures of 50-140° C. to give compounds of the formula (XIV)

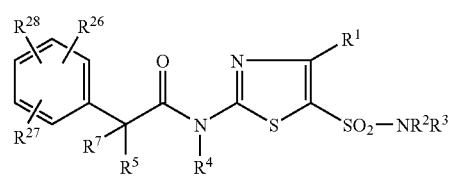

(XIV)

and

[D] reacting compounds of the general formula (XII)

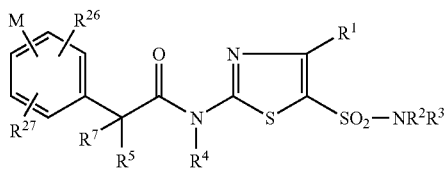

in which
R¹, R², R³, R⁴, R⁵, R⁷, R²⁶ and R²⁷ have the abovementioned meaning, and M has the abovementioned meaning, with trifluoromethanesulfonates or halides of the general formula (XIII):

R²⁸E  (XIII)

in which
R²⁸ has the abovementioned meaning, and E has the abovementioned meaning, in inert solvents in the presence of palladium catalysts, e.g. tetrakis-(triphenylphosphane) palladium (0), where appropriate in the presence of base, e.g. potassium phosphate at temperatures of 50-140° C. to give compounds of the formula (XIV).

Process [A] of the invention can be illustrated by way of example by the following formula diagrams:

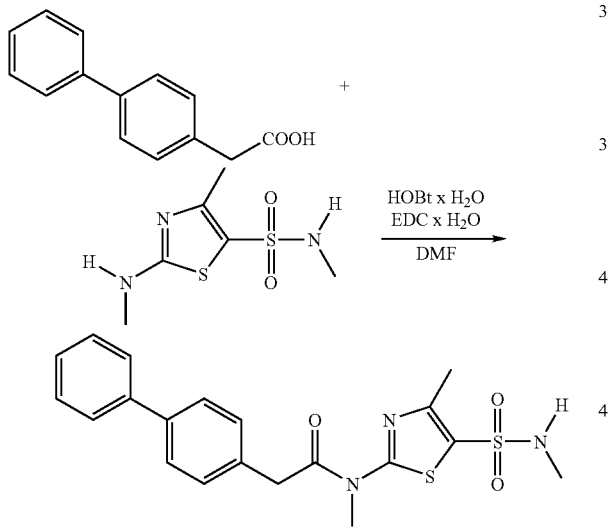

The meanings here are:
HOBt: 1-Hydroxy-1H-benzotriazole
EDC: N'-(3-Dimethylaminopropyl)-N-ethylcarbodiimide× HCl
DMF: N,N-Dimethylformamide Process [C] of the invention can be illustrated by way of example by the following formula diagrams:

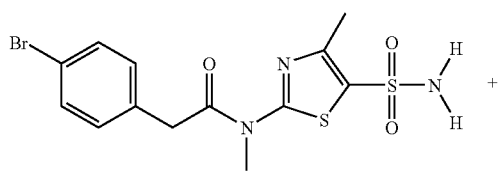

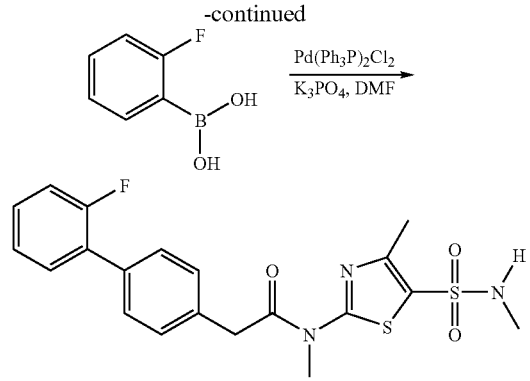

The meaning here is:
DMF: N,N-Dimethylformamide

Process [D] of the invention can be illustrated by way of example by the following formula diagrams:

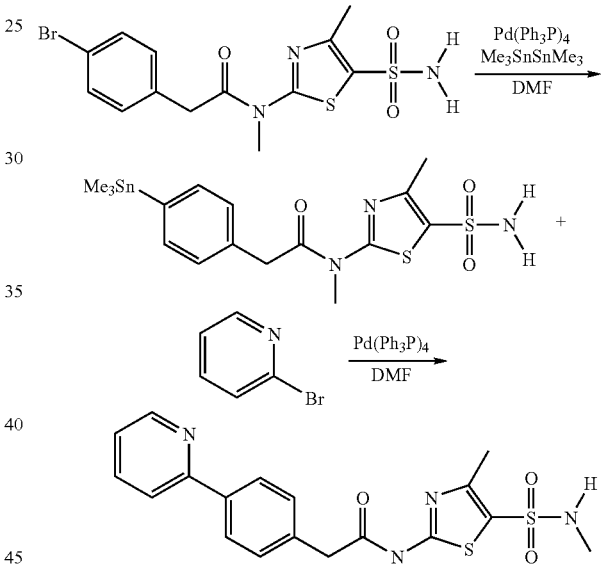

The meaning here is:
DMF: N,N-Dimethylformamide

Solvents suitable for processes [A], [B], [C] and [D] are conventional organic solvents which are not changed under the reaction conditions. These preferably include ethers such as diethyl ether, dioxane, tetrahydrofuran, glycol dimethyl ether, or hydrocarbons such as benzene, toluene, xylene, hexane, cyclohexane or petroleum fractions, or halohydrocarbons such as dichloromethane, trichloromethane, tetrachloromethane, dichloroethylene, trichloroethylene or chlorobenzene, or ethyl acetate, dimethyl sulfoxide, dimethyl formamide (DMF) or acetonitrile. It is likewise possible to use mixtures of said solvents. DMF is preferred.

Bases which can generally be employed for process [A] of the invention are inorganic or organic bases. These preferably include organic amines (trialkyl($C_1$-$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, N-methylmorpholine or N-methylpiperidine or morpholine. Triethylamine is preferred.

Suitable auxiliaries are dehydrating or coupling reagents known per se, such as, for example, carbodiimides such as diisopropylcarbodiimide, dicyclohexylcarbodiimide (DCC) or N-(3-dimethylaminopropyl)-N'-ethylcarbodiimide (EDC), or carbonyl compounds such as carbonyldiimidazole (CDI) or isobutyl chloroformate, or 1,2-oxazolium compounds such as 2-ethyl-5-phenyl-1,2-oxazolium-3-sulfonate, or phosphorus compounds such as propanephosphonic anhydride, diphenylphosphoric azide, benzotriazolyl-N-oxytris (dimethylamino)phosphonium hexafluorophosphate (BOP), or uronium compounds such as O-benzotriazol-1-yl-N,N,N', N'-tetramethyluronium hexafluorophosphate (HBTU), or methanesulfonyl chloride, where appropriate in the presence of aids such as N-hydroxysuccinimide or N-hydroxybenzotriazole.

The base is generally employed in an amount of from 0.05 mol to 10 mol, preferably from 1 mol to 2 mol, based on 1 mol of the compound of the formula (III).

The processes of the invention are generally carried out in a temperature range from −50° C. to +100° C., preferably from −30° C. to +60° C.

The processes of the invention are generally carried out under atmospheric pressure. It is, however, also possible to carry out the process under elevated pressure or under reduced pressure (for example in a range from 0.5 to 5 bar).

The compounds of the general formula (II) can be prepared for example by converting compounds of the general formula (VI)

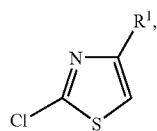
(VI)

in which
R$^1$ has the abovementioned meaning,
by reaction with the chlorosulfonic acid/SOCl$_2$ system into the compounds of the general formula (VII)

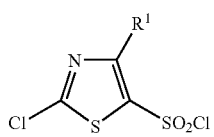
(VII)

in which
R$^1$ has the abovementioned meaning,
subsequently preparing with amines of the general formula (V)

HNR$^2$R$^3$ (V)

in which
R$^2$ and R$^3$ have the abovementioned meaning,
in inert solvents, the compounds of the general formula (VIII)

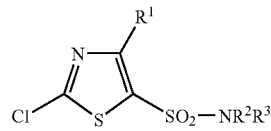
(VIII)

in which
R$^1$, R$^2$ and R$^3$ have the abovementioned meaning,
and in a last step carrying out a reaction with amines of the general formula (IX)

H$_2$N—R$^{4'}$ (IX)

in which
R$^{4'}$ has the abovementioned meaning of R$^4$ and is identical to or different from the latter, but is not hydrogen,
in inert solvents and in the presence of a base.

The reaction with chlorosulfonic acid/SO$_2$Cl takes place initially at room temperature and subsequently under the reflux temperature of the particular ether.

The reaction is generally carried out under atmospheric pressure. It is, however, also possible to carry out the process under elevated pressure or under reduced pressure (e.g. in a range from 0.5 to 5 bar).

Solvents suitable for the reaction with the amines of the general formula (V) are alcohols such as, for example, methanol, ethanol, propanol and isopropanol. Methanol is preferred.

The reaction with the amines of the general formula (V) takes place initially at room temperature and subsequently under the reflux temperature of the particular ether.

The reaction is generally carried out under atmospheric pressure. It is, however, also possible to carry out the process under elevated pressure or under reduced pressure (e.g. in a range from 0.5 to 5 bar).

The reaction with the compounds of the general formula (IX) takes place in ethers such as, for example, diethyl ether, dioxane, tetrahydrofuran or glycol dimethyl ether. Methanol is preferred.

Bases which can generally be employed are inorganic or organic bases. These preferably include organic amines (tri (C$_1$-C$_6$)alkylamines such as triethylamine), or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. Triethylamine is preferred.

The base is generally employed in an amount of from 0.05 mol to 10 mol, preferably from 1 mol to 2 mol, based on 1 mol of the compound of the formula (VIII).

The compounds of the general formula (VI) are in some cases known or can be prepared by conventional methods [cf. Hantzsch, Chem. Ber. 1927, 60, 2544].

The compounds of the general formula (VII) and (VIII) are novel and can be prepared as described above.

Amines of the general formulae (V) and (IX) are known.

Compounds of the general formulae (III) are known or can be prepared by processes known from the literature.

Biphenylmethylcarboxylic acid or biphenylacetic acid derivatives of the formula (III) can be prepared in a manner known per se by transition metal-catalyzed, for example palladium-catalyzed, coupling reactions such as, for example, the Suzuki or Stille coupling. The pyridylphenylmethylcarboxylic acid derivatives of the formula (III) are known from the literature (see, for example, M. Artico et al. *Eur. J. Med.*

*Chem.* (1992), 27, 219-228) or can be prepared by processes known per se. The following reaction schemes A, B, C and D illustrate by way of example the synthesis of biphenylacetic acid derivatives from the corresponding boronic acids, and the synthesis of pyridylphenyl acetic acid derivatives from the corresponding stannyl compounds:

A:

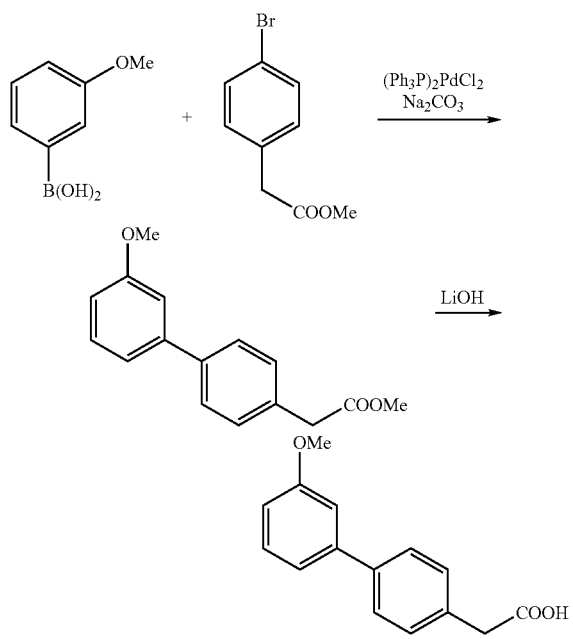

B:

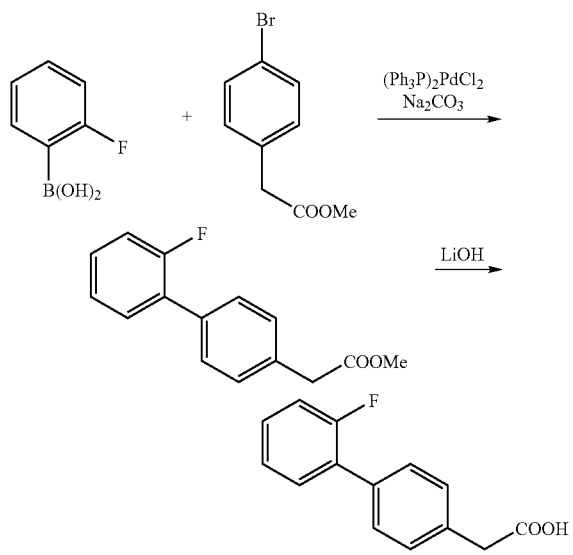

C:

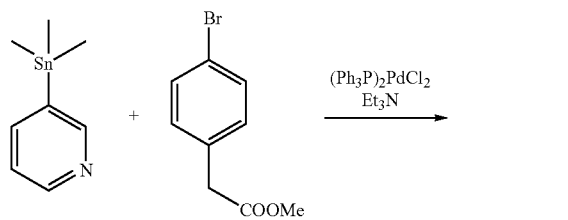

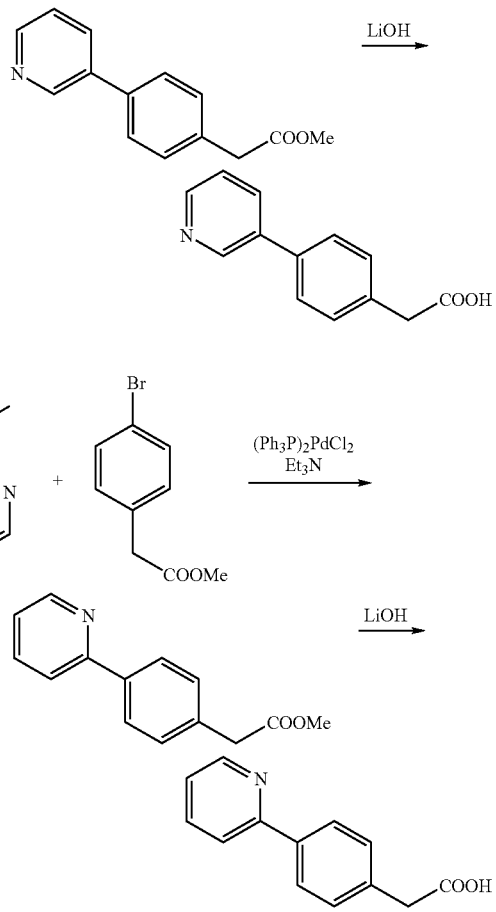

D:

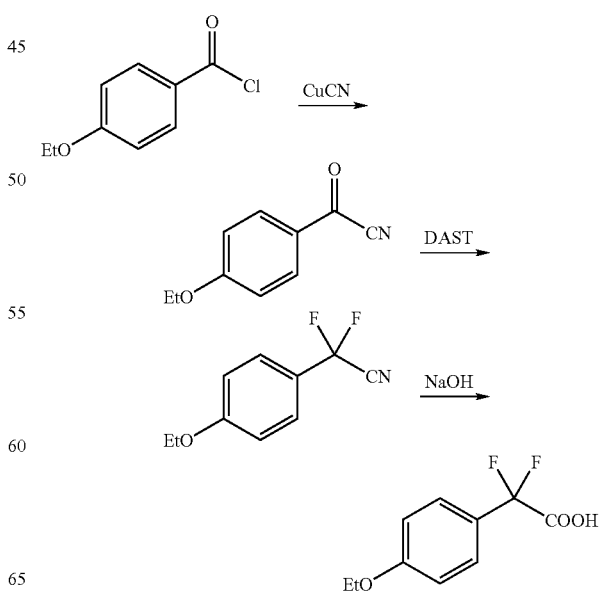

Compounds of the formula (III) in which $R^5$ and $R^7$ is, for example, fluorine can be prepared by the process shown in the following reaction scheme:

The fluorination with DAST (N,N-diethylaminosulfur trifluoride) in this case takes place as described in J. Fluor. Chem. 61, 1993, 117.

The present invention therefore relates to substituted thiazolylamides for topical application. In a further embodiment, the present invention relates to topical application to the skin, eye or vagina. Anhydrous preparations have proved very suitable, especially anhydrous and nongreasy preparations. Particular preference is given to the "PEG isogels" which will be defined in detail. It has emerged that herpes prophylaxis can also be achieved in the genital area with these preparations.

Formulation of the Active Ingredients

Ophthalmological Topical Application

To form a 2% by weight suspension, the active ingredients are mixed with Liquifilm eyedrops (Allergan, Ettlingen, Germany) (1 ml containing polyvinyl alcohol 14 mg, and as excipient chlorobutanol ½ $H_2O$ 5.25 mg, sodium chloride) and sonified in a glass tube in an ultrasonic bath at 15° C. for 15 min.

Dermatological Topical Application

1) Alcoholic Suspension

To form a 2% by weight suspension, the active ingredients are mixed with 30% by weight isopropyl myristate/70% by weight of ethanol and sonified in a glass tube in an ultrasonic bath at 15° C. for 15 min.

2) Spreadable Preparations

To produce the ointment preparation, wool alcohol ointment complying with DAB 9 is employed. The active ingredient is suspended in a molten mixture of 0.5 parts by weight of cetyl stearyl alcohol (quality complying with DAB 9), 6 parts by weight of wool wax alcohol (quality complying with DAB 9) and 93.5 parts by weight of white petrolatum (quality complying with DAB 9). The mixture is stirred while cooling to room temperature (about 21° C.).

To produce a so-called "PEG isogel" preparation, the active ingredient is suspended or dissolved in the melt a mixture of lower molecular weight polyethylene glycol (PEG) and higher molecular weight PEG.

After the active ingredient has been suspended or dissolved in the melt, the preparation is stirred while cooling to room temperature.

Lower molecular weight PEG is liquid at room temperature (about 21° C.), and higher molecular weight PEG is solid (can be cut, wax-like) at room temperature.

The mixture ratios of the two PEG types depend on the required viscosity of the preparation and on the average molecular weights of the PEG types employed.

Examples which can be used are preparations composed of 6.5 parts by weight of PEG 400 and 1 part by weight of PEG 4000 or 7 parts by weight of PEG 400 and 2 parts by weight of PEG 6000. Mixing ranges vary from 1:1 to 10:1 (in each case parts by weight of lower molecular weight PEG to higher molecular weight PEG. The range from 2:1 to 8:1 is preferred, and the range from 3:1 to 7:1 is particularly preferred.

A further gel preparation employed is a polyacrylate gel (so-called "carbogel") which consists of 1 part by weight of Carbopol 974 P NF (manufacturer BF Goodrich, USA), parts by weight of isopropyl alcohol, 5 part by weight of 5% by weight (m/m) sodium hydroxide solution and 89 parts by weight of water. The preparation is produced by rubbing the Carbopol with the isopropanol, adding the active ingredient, and dispersing the mixture in water. The sodium hydroxide solution is added stepwise with stirring. A gel is formed.

In Vivo Effect

Ocular Herpes Model 6-week old female mice, strain BALB/cABom (weight 19 g) are purchased from a commercial breeder (M&B A/S, Denmark) and infected with HSV one week later. The animals are anesthetized in a leakproof glass vessel with diethyl ether (Merck). For the ocular infection, the cornea of the right eye is lightly scratched three times horizontally and three times vertically with a sterile needle (0.4×20 mm). The cornea pretreated in this way is inoculated with 5 µl of virus suspension ($5 \times 10^7$ pfu HSV-2G, $7.5 \times 10^7$ pfu HSV-lwalki). The infected animals are checked each day and examined for signs of an HSV infection (blepharitis, keratitis, encephalitis). The pathology index is set at 1 for affected animals, and the pathology index is set at 0 for symptom-free animals. The particular pathology index of the group on the particular day is calculated by summation for all the animals in the group. The cumulative pathology index is calculated by totalling the pathology indices on individual days. The infection leads to the death of 90-100% of untreated animals due to a generalized infection with prominent central nervous symptoms an average of between 5 and 8 days. Moribund animals are euthanized. The treatment takes place starting 3 h after the infection 5× a day for 5 days by instilling 5 µl of a 2% by weight active ingredient suspension in Liquifilm© eye drops (Allergan, Ettlingen, Germany) (1 ml containing polyvinyl alcohol 14 mg, and as excipient chlorobutanol ½ $H_2O$ 5.25 mg, sodium chloride) into the infected right eye of the animal.

Zosteriform Spread Model 6-week old female hairless mice (C3H/TifBom-hr) are purchased from a commercial breeder (M&B A/S, Denmark) and infected with HSV one week later. The animals are anesthetized with diethyl ether (Merck) in a leakproof glass vessel. For the dermal infection, the skin on the right flank or in the neck region of the animal is scratched 10× crosswise with a sterile needle (0.6×25 mm). The skin pretreated in this way is inoculated with 10 µl of virus suspension ($1 \times 10^6$ pfu HSV-2G; $1.5 \times 10^6$ p fu HSV-lwalki). The animals are inspected each day, and the pathology index is determined by means of the following scale: 0: no visible signs of infection, 1: blistering, 2: slight spread in the dermatome (shingles), 3: large areas affected (shingles), 4: confluent shingles bands, 5: paralysis of the extremities, 6: death. The particular pathology index of the group on the particular day is calculated by forming the average for all the animals in the group. The cumulative pathology index is calculated by totalling the pathology indices for individual days. The infection leads to death of 90-100% of the untreated animals due to a generalized infection with prominent central nervous symptoms an average of between 5 and 8 days. Moribund animals are euthanized. The treatment takes place starting 6 h after the infection 3× a day for 5 days by rubbing an active ingredient-containing formulation into the infected region of the body.

EXAMPLES

Example 1

Effect on Topical Treatment in the Ocular Herpes Model (Ophthalmological Application)

Topical treatment (eye drops) of animals with ocular HSV infection surprisingly shows an extensive efficacy of the thiazolylamides (represented by examples of N-[5-(aminosulfonyl)-4-methyl-1,3-thiazol-2-yl]-N-methyl-2-[4-(2-pyridyl)phenyl]-acetamide and N-[5-(aminosulfonyl)-4-methyl-1,3- thiazol-2-yl]-2-(2',5'-difluoro-1,1'-biphenyl-4-yl)-N-methylacetamide. A marked superiority is evident on comparison with the current therapeutic standard Zovirax©. This applies both to the occurrence of pathological manifestations on the eye itself (blepharitis, keratitis) and to the prevention of spread of a generalized herpes infection in the infected animal (encephalitis and death). The efficacy applies to infections with HSV-1 and HSV-2.

Table 1 shows the number of survivors of 10 infected animals, day 16 after the infection, with topical ophthalmic application (from day 0 to day 4 after the infection) of 2% by weight suspensions of the stated substances 5× a day.

TABLE 1

| Substance | HSV-1 | HSV-2 |
|---|---|---|
| Placebo | 0 | 0 |
| Aciclovir © | 7 | 1 |
| N-[5-(aminosulfonyl)-4-methyl-1,3-thiazol-2-yl]-N-methyl-2-[4-(2-pyridyl)phenyl]acetamide | 10 | 9 |
| N-[5-(aminosulfonyl)-4-methyl-1,3-thiazol-2-yl]-2-(2',5'-difluoro-1,1'-biphenyl-4-yl)-N-methylacetamide | 10 | 4 |

Table 2 shows the cumulative pathology index from day 0 to day 16 after the infection of 10 animals with topical ophthalmic application (from day 0 to day 4 after the infection) of 2% by weight suspensions of the stated substances 5× a day.

TABLE 2

| Substance | Pathology index HSV-1 infection | Pathology index HSV-2 infection |
|---|---|---|
| Placebo | 120 | 132 |
| Aciclovir | 33 | 90 |
| N-[5-(aminosulfonyl)-4-methyl-1,3-thiazol-2-yl]-N-methyl-2-[4-(2-pyridyl)phenyl]acetamide | 0 | 7 |
| N-[5-(aminosulfonyl)-4-methyl-1,3-thiazol-2-yl]-2-(2',5'-difluoro-1,1'-biphenyl-4-yl)-N-methylacetamide | 0 | 42 |

Example 2

Effect of Topical Treatment in the Zosteriform Spread Model

Topical treatment (2% by weight active ingredient suspension in 30% by weight isopropyl myristate, 70% by weight ethanol) of animals infected percutaneously on the right flank with HSV-2 surprisingly shows an extensive efficacy of the thiazolylamides (represented by the examples of N-[5-(aminosulfonyl)-4-methyl-1,3-thiazol-2-yl]-2-[1,1'-biphenyl]-4-yl-N-methylacetamide N-[5-(aminosulfonyl)-4-methyl-1,3-thiazol-2-yl]-2-(2'-fluoro [1,1'-biphenyl]4-yl)-N-methylacetamide N-[5-(aminosulfonyl)-4-methyl-1,3-thiazol-2-yl]-2-(3'-fluoro-1,1'-biphenyl-4-yl)-N-methylacetamide N-[5-(aminosulfonyl)-4-methyl-1,3-thiazol-2-yl]-N-methyl-2-[4-(2-pyridyl)phenyl]acetamide A marked superiority is evident by comparison with the current therapeutic standard Zovirax.

Table 3 shows the cumulative pathology index from day 0 to day 21 after infection of 10 animals with topical application onto the skin (from day 0 to day 4 after the infection) of 2% by weight suspensions of the stated substances 2× a day.

TABLE 3

| Substance | Pathology index |
|---|---|
| Placebo | 101.4 |
| Aciclovir | 37.5 |
| N-[5-(aminosulfonyl)-4-methyl-1,3-thiazol-2-yl]-2-(1,1'-biphenyl-4-yl)-N-methylacetamide | 7.9 |
| N-[5-(aminosulfonyl)-4-methyl-1,3-thiazol-2-yl]-2-(2'-fluoro-1,1'-biphenyl-4-yl)-N-methylacetamide | 0.2 |
| N-[5-(aminosulfonyl)-4-methyl-1,3-thiazol-2-yl]-2-(3'-fluoro-1,1'-biphenyl-4-yl)-N-methylacetamide | 0.3 |
| N-[5-(aminosulfonyl)-4-methyl-1,3-thiazol-2-yl]-N-methyl-2-[4-(2-pyridyl)phenyl]acetamide. | 0.3 |

Example 3

Effect of Topical Treatment with Various Formulations

The preparations employed are:

3% by weight (m/m) active ingredient in wool alcohol ointment DAB 9 (for composition and production, see "spreadable preparations").

3% by weight (m/m) active ingredient in PEG isogel (composed of 6.5 part by weight of PEG 400 and 1 part by weight of PEG 4000, for production, see "spreadable preparations").

3% by weight (m/m) active ingredient in polyacrylate gel (so-called carbogel) (for production, see "spreadable preparations").

an active ingredient-free PEG isogel (composed of 6.5 part by weight of PEG 400 and 1 part by weight of PEG 4000, for production, see "spreadable preparations", but no active ingredient is incorporated) serves as placebo control.

The topical treatment (various formulations with 3% by weight active ingredient content) of animals infected percutaneously in the neck region with HSV-2G (housed singly) surprisingly showed an extensive efficacy of the thiazolylamides (represented by the example of N-[5-(aminosulfonyl)-4-methyl-1,3-thiazol-2-yl]-N-methyl-2-[4-(2-pyridyl)phenyl]acetamide) with all the tested formulations. The N-[5-(aminosulfonyl)-4-methyl-1,3-thiazol-2-yl]-N-methyl-2-[4-(2-pyridyl)phenyl]acetamide PEG isogel formulation, and the formulation with wool alcohol, is superior to the Zovirax© eye ointment (Glaxo Wellcome®). Table 4 shows the cumulative pathology index from day 0 to day 21 after infection of 10 animals with topical application to the skin (from day 0 to day 4 after the infection) of 3% by weight formulations of the stated substance 2× a day.

TABLE 4

| Substance | Pathology index |
|---|---|
| Untreated | 99 |
| PEG isogel placebo | 101 |
| N-[5-(aminosulfonyl)-4-methyl-1,3-thiazol-2-yl]-N-methyl-2-[4-(2-pyridyl)phenyl]acetamide Wool alcohol | 1.1 |
| N-[5-(aminosulfonyl)-4-methyl-1,3-thiazol-2-yl]-N-methyl-2-[4-(2-pyridyl)phenyl]acetamide PEG isogel | 0.4 |
| N-[5-(aminosulfonyl)-4-methyl-1,3-thiazol-2-yl]-N-methyl-2-[4-(2-pyridyl)phenyl]acetamide Carbogel | 10 |
| Zovirax © eye ointment (aciclovir) | 3.6 |

Example 4

Effect of Topical Treatment for 2 Days

The preparations employed are:

2% by weight (m/m) active ingredient in PEG isogel (composed of 6.5 part by weight of PEG 400 and 1 part by weight of PEG 4000, for production see "spreadable preparations").

An active ingredient-free PEG isogel (composed of 6.5 part by weight of PEG 400 and 1 part by weight of PEG 4000, for production see "spreadable preparations", but no active ingredient is incorporated) serves as placebo control.

Topical treatment (2% by weight active ingredient content, PEG isogel) of animals infected percutaneously in the neck region with HSV-2G (housed singly) surprisingly shows an extensive efficacy of only short treatments (2× a day for 2 days) with the thiazolylamides (represented by the example of N-[5-aminosulfonyl)-4-methyl-1,3-thiazol-2-yl]-N-methyl-2-[4-(2-pyridyl)phenyl]acetamide. This experiment once again clearly illustrates the excellent topical efficacy of the substances. An infection which leads to death of all the experimental animals without treatment is completely suppressed by only 4 treatments. Table 5 shows the cumulative pathology index from day 0 to day 21 after the infection of 10 animals with topical application to the skin (from day 0 to day 1 after the infection) of 2% by weight formulations of the stated substance 2× a day.

TABLE 5

| Substance | Pathology index |
|---|---|
| Placebo | 96.9 |
| N-[5-(aminosulfonyl)-4-methyl-1,3-thiazol-2-yl]-N-methyl-2-[4-(2-pyridyl)phenyl]acetamide | 0.3 |

Starting Compounds

Example I

2-Chloro-4-methyl-1,3-thiazole-5-sulfonyl chloride

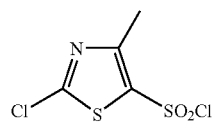

150 g (1.12 mol) of 2-chloro-4-methyl-1,3-thiazole are added dropwise at room temperature to a solution of 331 g (2.81 mmol) of thionyl chloride in 653 g (5.61 mmol) of chlorosulfonic acid. The solution is heated to reflux for 48 h. The mixture is then added to 3 l of ice-water and extracted with 4×400 ml of dichloromethane. The combined organic phases are washed with 2.5 l of water, dried over sodium sulfate and concentrated. Distillation of the crude product results in 233.7 g of product in the form of an oil. (Boiling point 87-96° C., 0.7 mbar, GC 98.1%, yield 89.6%).

Example II

2-Chloro-4-methyl-1,3-thiazole-5-sulfonamide

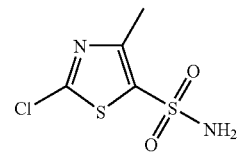

117.7 g (1.8 mol) of 26% strength aqueous ammonia solution are added dropwise to a solution of 208 g (95% pure, 0.9 mol) of 2-chloro-4-methyl-1,3-thiazole-5-sulfonyl chloride in 1000 ml of tetrahydrofuran at −10° C. The reaction mixture is left to stir without further cooling for 2 h and is then concentrated in a rotary evaporator. The crude product is employed without further purification in the next stage.

Example III

4-Methyl-2-(methylamino)-1,3-thiazole-5-sulfonamide

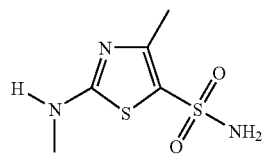

144 g (0.576 mol) of 2-chloro-4-methyl-1,3-thiazole-5-sulfonamide are introduced at room temperature into 600 ml of acetonitrile, and 147 g (1.9 mol) of 40% strength aqueous methylamine solution are metered in at room temperature. The reaction mixture is stirred at 50° C. for 6 h and then concentrated in a rotary evaporator. The residue is mixed with water, filtered with suction and dried.

Yield: 78 g (66%)

Melting point: 194° C.

Example IV

2-Fluorophenylboronic acid

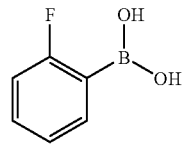

155 g (0.86 mol) of 2-fluorobromobenzene are introduced under argon into 732 ml of absolute tetrahydrofuran and, at −78° C., 600 ml of 1.6 M n-butyllithium in hexane are slowly added. The mixture is then stirred at −78° C. for 2 h. Subsequently 298 ml (1.28 mol) of trimethyl borate are added dropwise at −78° C. After 1 h, the cooling is removed and the reaction mixture is stirred and warmed to room temperature overnight. The mixture is worked up by adding 346 ml of saturated ammonium chloride solution at 0° C., adjusting the pH to 6 with 1N HCl, and extracting the aqueous phase 3 times with 250 ml of methylene chloride each time. The combined organic phases are washed with saturated sodium chloride solution and dried with magnesium sulfate. Example IV is obtained in the form of a beige solid.

Yield: 60.0 g (48%)

MS (EI, m/z): 140 (80%, [M]$^+$), 96 (100%, [C$_6$H$_5$F]$^+$)

Example V

Methyl (2'-fluoro[1,1'-biphenyl]-4-yl)acetate

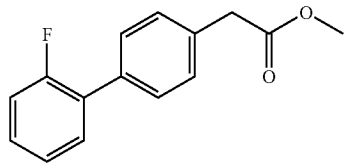

47.6 g (0.21 mol) of methyl 4-bromophenylacetate are introduced under argon into 400 ml of absolute tetrahydrofuran and, at room temperature, 320 ml of 1M sodium carbonate solution and 40 g (0.28 mol) of 2-fluorophenylboronic acid are added. Addition of 7.0 g (0.01 mol) of bis(triphenylphosphane)palladium(II) chloride is followed by heating under reflux for 18 h. Cooling is followed by dilution with 500 ml of water and extracted three times with 300 ml of ethyl acetate each time. The combined organic phases are washed with 400 ml each of saturated ammonium chloride solution, water and saturated sodium chloride solution, dried over magnesium sulfate and freed of solvent in vacuo. Example V is obtained after silica gel filtration (petroleum ether/ethyl acetate 10:1) as a colorless oil.

Yield: 46.0 g (94%)

$^1$H NMR (500 MHz, CDCl$_3$, δ/ppm): 3.71 (s, 2H), 3.76 (s, 3H), 7.18-7.46 (m, 4H), 7.40 (d, J=8.3 Hz; 2H), 7.56 (dd, J$_1$=8.3 Hz, J$_2$=1.7 Hz; 2H).

Example VI (2'-Fluoro[1,1'-biphenyl]4-yl)acetic acid

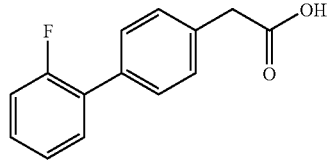

26.5 g (0.11 mol) of methyl (2'-fluoro[1,1'-biphenyl]4-yl) acetate are introduced into 50 ml of ethanol and, at room temperature, a solution of 12.8 g (0.19 mol) of potassium hydroxide pellets in 25 ml of water is added. The mixture is then heated under reflux for 4 h. After cooling, the crude mixture is concentrated in vacuo, and the residue is dissolved in 100 ml of water and acidified with concentrated hydrochloric acid. The precipitate is filtered off and washed several times with water, and the solid is dried. Example VI is obtained in the form of white crystals.

Yield: 22.7 g (91%)

Melting point: 102° C.

$^1$H NMR (500 MHz, CDCl$_3$, δ/ppm): 3.74 (s, 2H), 7.18-7.47 (m, 4H, 7.41 (d, J=8.2 Hz; 2H), 7.57 (dd, J$_1$=8.2 Hz, J$_2$=1.6 Hz; 2H).

Example VII

Methyl [4-(2-pyridyl)phenyl]acetate

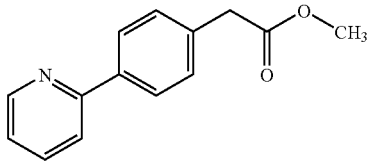

7.85 g (34.3 mmol) of methyl 4-bromophenylacetate are introduced under argon into 95 ml of toluene and, at room temperature, 7.97 g (61.7 mmol) of diisopropylethylamine, 9.50 g (37.7 mmol) of 2-trimethylstannylpyridine and 0.4 g (0.3 mmol) of tetrakis(triphenylphosphane)palladium(0) are added. The mixture is then heated under reflux for 18 h. Cooling is followed by washing with 100 ml each of 1N hydrochloric acid and saturated sodium bicarbonate solution. The organic phase was discarded. The acidic and the basic aqueous phase were neutralized and each extracted with 100 ml of dichloromethane, and the combined organic phases were dried over magnesium sulfate and freed of solvent in vacuo. Example VII is obtained after silica gel chromatography (toluene/ethyl acetate gradient 5: 1-1:1) as a colorless oil.

Yield: 1.6 g (19%)

$^1$H NMR (400 MHz, d$^6$-DMSO, δ/ppm): 3.64 (s, 3H), 3.76 (s, 2H), 7.33-7.40 (m, 1H), 7.39 (d, J=8.2 Hz; 2H), 7.86-7.90 (m, 1H), 7.96 (d, J=8.0 Hz; 1H), 8.05 (d, J=8.2 Hz; 2H), 8.67 (d, J=4.2 Hz, broad; 1H).

Example VIII

[4-(2-pyridyl)phenyl]acetic acid

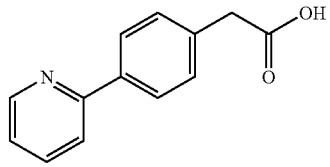

700 mg (3.11 mol) of methyl [4-(2-pyridyl)phenyl]acetate are introduced into 5 ml of tetrahydrofuran and, at room temperature, 6.2 ml of a 1M potassium hydroxide solution in water are added. The mixture is stirred at room temperature for 18 h and then the solvent is substantially removed in vacuo, the residue is taken up in 10 ml of water and the pH was adjusted to about 5 with 2N hydrochloric acid. Extraction of the aqueous phase twice with 10 ml of dichloromethane each time affords, after drying the combined organic phases over magnesiumsulfate and removing the solvent in vacuo, the compound of Example VIII in the form of a solid.

Yield: 300 mg (46%)

$^1$H NMR (400 MHz, d$^6$-DMSO, δ/ppm): 3.76 (s, 2H), 7.45-7.51 (m, 1H), 7.50 (d, J=8.3 Hz; 2H), 8.00 (td, J$_1$=7.7

Hz, $J_2$=1.9 Hz; 1H), 8.07 (d, J=7.9 Hz, 1H), 8.15 (d, J=8.3 Hz; 2H), 8.78 (dt, $J_1$=4.0 Hz, $J_2$=0.9 Hz; 1H).

PREPARATION EXAMPLES

Example 15

N-[5-Aminosulfonyl)-4-methyl-1,3-thiazol-2-yl]-2-[1,1'-biphenyl]-4-yl-N-methylacetamide

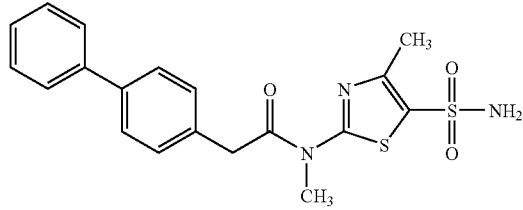

138.2 mg (0.65 mmol) of 4-biphenylacetic acid and 99.7 mg (0.65 mmol) of 1-hydroxy-1H-benzotriazole hydrate are introduced into 5 ml of dimethylformamide at room temperature. 150 mg (0.72 mmol) of 2-methylamino-4-methyl-1,3-thiazole-5-sulfonamide and 138.7 mg (0.72 mmol) of N'-(3-dimethylaminopropyl)-N-ethylcarbodiimide hydrochloride are added, and the mixture is stirred at room temperature for 72 h. The reaction mixture is then filtered with suction and the residue is recrystallized from 2-propanol. A white solid is obtained.

Yield: 240 mg (83.0%)
Melting point: 191° C.
$^1$H NMR (300 MHz, $d^6$-DMSO, δ/ppm): 2.47 (s, 3H; partly underneath DMSO signal), 3.71 (s, 3H), 4.20 (s, 2H), 7.32-7.70 (m, 11H).

Example 38

N-[5-(Aminosulfonyl)-4-methyl-1,3-thiazol-2-yl]-N-methyl-2-[4-(2-pyridyl)phenyl]acetamide

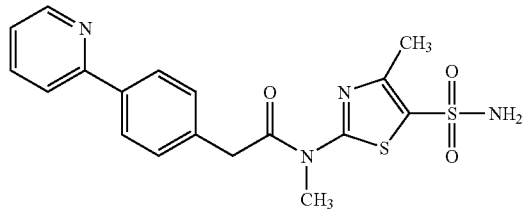

300 mg (1.41 mmol) of [4-(2-pyridyl)phenyl]acetic acid and 190 mg (1.41 mmol) of 1-hydroxy-1H-benzotriazole hydrate are introduced into 4 ml of dimethylformamide at room temperature. 307 mg (1.48 mmol) of 2-methylamino-4-methyl-1,3-thiazole-5-sulfonamide and 284 mg (1.48 mmol) of N'-(3-dimethylaminopropyl)-N-ethylcarbodiimide hydrochloride are added, and the mixture is stirred at room temperature for 18 h. The solvent is then removed in vacuo, the residue is taken up in toluene, and the solvent is again removed in vacuo. The residue is stirred with 15 ml of water and 3 ml of methanol and then filtered off, and the filtrate is back-extracted with 20 ml of dichloromethane. Solid and dichloromethane phase are combined, and the solvent is removed in vacuo. The compound of Example 38 is obtained in the form of a white solid.

Yield: 440 mg (74.0%)
Melting point: 188-192° C.
MS (ESI, m/z): 403 (100%, [M+H]$^+$)
$^1$H NMR (400 MHz, $d^6$-DMSO, δ/ppm): 2.38 (s, 3H; underneath DMSO signal), 3.64 (s, 3H), 4.15 (s, 2H), 7.28-7.26 (m, 1H), 7.32 (d, J=8 Hz; 2H), 7.58 (s, 2H), 7.82-7.96 (m, 2H), 7.98 (d, J=8.0 Hz; 2H), 8.61 (m; 1H).

Example 57

N-[5-(Aminosulfonyl)-4-methyl-1,3-thiazol-2-yl]-2-(2'-fluoro[1,1'-biphenyl]-4-yl)-N-methylacetamide

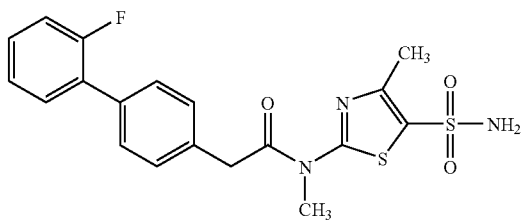

17.33 g (73.3 mmol) of (2'-fluoro[1,1'-biphenyl]-4-yl)acetic acid and 9.9 g (73.3 mmol) of 1-hydroxy-1H-benzotriazole hydrate are introduced into 600 ml of dimethylformamide at room temperature. 16.84 g (81.4 mmol) of 2-methylamino-4-methyl-1,3-thiazole-5-sulfonamide and 15.58 g (81.4 mmol) of N'-(3-dimethylaminopropyl)-N-ethylcarbodiimide hydrochloride are added, and the mixture is stirred at room temperature for 18 h. The dimethylformamide is substantially removed at 50° C. under high vacuum, and the residue is taken up in 400 ml of dichloromethane and then washed with 350 ml of each of water and 10% citric acid solution. Drying over magnesium sulfate and removal of the solvent in vacuo results in the compound of Example 57 in the form of a white solid.

Yield: 23.2 g (76.0%)
Melting point: 211° C.
$^1$H NMR (400 MHz, $CDCl_3$, δ/ppm): 2.58 (s, 3H), 3.73 (s, 3H), 4.07 (s, 2H), 5.91 (s, 2H), 7.13-7.46 (m, 4H), 7.34 (d, J=8.1 Hz; 2H), 7.56 (d, broad, J=8.1 Hz; 2H).

Example 87

N-[5-(Aminosulfonyl)-4-methyl-1,3-thiazol-2-yl]-2-(2',5'-difluoro-1,1'-biphenyl-4-yl)-N-methylacetamide

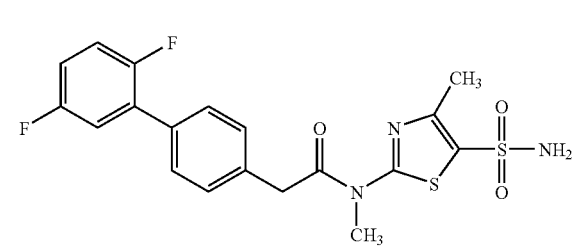

1.00 g (4.0 mmol) of (2',5'-difluoro[1,1'-biphenyl]-4-yl) acetic acid and 0.54 g (4.0 mmol) of 1-hydroxy-1H-benzotriazole hydrate are introduced into 15 ml of dimethylformamide at room temperature. 0.84 g (4.0 mmol) of 2-methylamino-4-methyl-1,3-thiazole-5-sulfonamide and 0.77 g (4.0 mmol) of N'-(3-dimethylaminopropyl)-N-ethyl-carbodiimide hydrochloride are added, and the mixture is stirred at room temperature for 18 h. The dimethylformamide is substantially removed at 50° C. under high vacuum, and the residue is stirred 3 times with 50 ml of water each time, filtered off, stirred with 50 ml of isopropanol and again filtered off. Removal of the solvent in vacuo results in the compound of Example 87 in the form of a pale yellow-colored solid.

Yield: 0.83 g (47.3%)

Melting point: 184° C.

$^1$H NMR (400 MHz, DMSO, δ/ppm): 2.49 (s, 3H), 3.71 (s, 3H), 4.24 (s, 2H), 7.22-7.46 (m, 3H), 7.38 (d, J=8.2 Hz; 2H), 7.56 (d, J=8.2 Hz; 2H), 7.65 (s, 2H).

Example 126

N-[5-(Aminosulfonyl)-4-methyl-1,3-thiazol-2-yl]-N-methyl-2-[4-(1H-pyrazol-1-yl)phenyl]acetamide

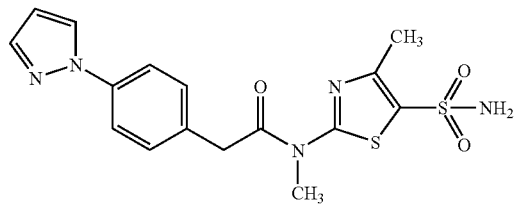

0.100 g (0.48 mmol) of 2-methylamino-4-methyl-1,3-thiazole-5-sulfonamide is dissolved in 10 ml of N,N-dimethylformamide and, at room temperature, 0.110 g (0.53 mmol) of [4-(1H-pyrazol-1-yl)phenyl]acetic acid, 0.070 g (0.53 mmol) of 1-hydroxy-1H-benzotriazole and 0.070 g (0.53 mmol) of N,N'-diisopropylcarbodiimide are added. The solution is stirred at room temperature overnight. The mixture is then poured into water, and the aqueous phase is extracted three times with ethyl acetate. The combined organic phases are dried with sodium sulfate and concentrated. The crude product is finally purified by preparative HPLC (RP18 column; mobile phase; acetonitrile/water gradient).

Yield: 0.11 g (59%)

LC-MS (method: SMKL-N1-1Low Vol HCl): retention time: 3.65

MS (ESI): 783 (2Mz+H), 392 (Mz+H).

$^1$H NMR (300 MHz, DMSO, δ/ppm): 2.48 (s, 3H), 3.72 (s, 3H), 4.20 (s, 2H), 6.55 (t, J=2 Hz, 1H), 7.38 (d, J=7 Hz; 2H), 7.65 (s, 2H), 7.75 (d, J=2 Hz; 1H), 7.82 (d, J=7 Hz; 2H), 8.49 (d, J=2 Hz; 1H).

Example 127

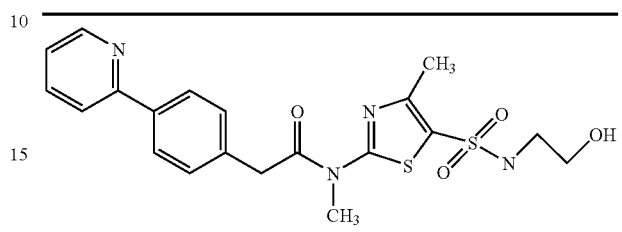

| Method: | SMKL-N1 |
|---|---|
| MS apparatus type: | Finnigan MAT 900S |
| | Ionization: ESI positive |
| HPLC apparatus type: | TSP: P4000, AS3000, UV3000HR |
| Pump head: | normal |
| Column: | Symmetry C 18 |
| | 150 mm × 2.1 mm 5 µm |
| Supplying company: | Waters |
| UV detector DAD: | 210 nm |
| Oven temp.: | 40° C. |

| Gradient: | Time | A:% | B:% | C:% | D:% | Flow |
|---|---|---|---|---|---|---|
| | 0 | 10.0 | 45 | 45 | — | 0.6 |
| | 4 | 90 | 5 | 5 | — | 0.6 |
| | 9 | 90 | 5 | 5 | — | 0.6 |
| | 9.5 | 10.0 | 45 | 45 | — | 0.8 |
| | 11.5 | 10.0 | 45 | 45 | — | 0.8 |
| | 12 | 10.0 | 45 | 45 | — | 0.6 |

A:CH$_3$CN
B:HCl 0.01 N
C:H$_2$O
D:—

The invention claimed is:

1. A topically applicable preparation comprising from 0.1 to 99% by weight of a compound of formula (I) having the structure:

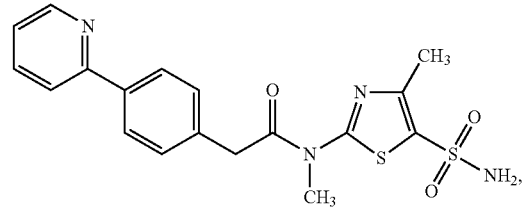

and a wool alcohol ointment.

2. The preparation of claim 1, comprising from 0.5 to 20% by weight of the compound of formula (I) according to claim 1.

3. The preparation of claim 1, comprising from 1 to 5% by weight of the compound of formula (I) according to claim 1.

4. The preparation of claim 1, comprising from 2 to 3% by weight of the compound of formula (I) according to claim 1.

5. The preparation of claim 1, in the form of a suspension or ointment.

* * * * *